United States Patent [19]

Husbands et al.

[11] Patent Number: 4,611,078

[45] Date of Patent: Sep. 9, 1986

[54] SUBSTITUTED PHENYLACETONITRILES

[75] Inventors: G. E. Morris Husbands, Berwyn; John P. Yardley, Gulph Mills; Eric A. Muth, West Chester, all of Pa.

[73] Assignee: American Home Products Corporation, New York, N.Y.

[21] Appl. No.: 736,747

[22] Filed: May 22, 1985

Related U.S. Application Data

[60] Division of Ser. No. 545,701, Oct. 26, 1983, Pat. No. 4,535,186, which is a continuation-in-part of Ser. No. 486,594, Apr. 19, 1983, abandoned, which is a continuation-in-part of Ser. No. 449,032, Dec. 13, 1982, abandoned.

[51] Int. Cl.⁴ ............................................ C07C 121/75
[52] U.S. Cl. .................................. 558/410; 558/406
[58] Field of Search ................................. 558/406, 410

[56] References Cited

FOREIGN PATENT DOCUMENTS 1124485 3/1962 Fed. Rep. of Germany .
6408 10/1968 France .

OTHER PUBLICATIONS

Mutak et al., Acta Pharm. Jugosl. 31, 17 and 143 (1981).

Primary Examiner—Dolph H. Torrence
Attorney, Agent, or Firm—Richard K. Jackson

[57] ABSTRACT

This application discloses certain substituted phenylacetonitriles of the formula:

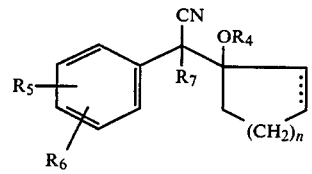

in which the dotted line represents optional unsaturation, and $R_4$ is hydrogen or alkyl;

$R_5$ and $R_6$, one of which may be hydrogen, are ortho or para substituents, independently selected from the group consisting of hydroxyl, alkyl, alkoxy, aralkoxy, alkanoyloxy, alkylmercapto, halo or trifluoromethyl;

$R_7$ is hydrogen or alkyl; and n is one of the integers 0, 1, 2, 3 or 4;

which are useful in the production of antidepressant agents.

5 Claims, No Drawings

SUBSTITUTED PHENYLACETONITRILES

This application is a division of U.S. patent application Ser. No. 545,701, filed Oct. 26, 1983, U.S. Pat. No. 4,535,186 which application is a continuation-in-part of U.S. patent application Ser. No. 486,594, filed Apr. 19, 1983, now abandoned, which application is a continuation-in-part of U.S. patent application Ser. No. 449,032, filed Dec. 13, 1982, now abandoned.

DESCRIPTION OF THE INVENTION

In accordance with this invention there is provided a group of substituted phenethylamine derivatives which are central nervous system antidepressants. The compounds of this invention present the following structural formula:

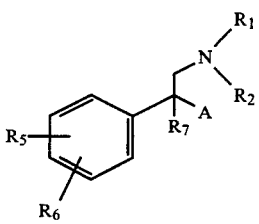

in which A is a moiety of the formula

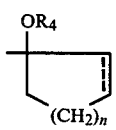

where the dotted line represents optional unsaturation, or the analogous cycloalkenyl moiety

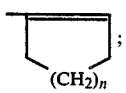

$R_1$ is hydrogen or alkyl of 1 to 6 carbon atoms;
$R_2$ is alkyl of 1 to 6 carbon atoms;
$R_4$ is hydrogen, alkyl of 1 to 6 carbon atoms, formyl, or alkanoyl of 2 to 7 carbon atoms;
$R_5$ and $R_6$ are independently hydrogen, hydroxyl, alkyl of 1 to 6 carbon atoms, alkoxy of 1 to 6 carbon atoms, alkanoyloxy of 2 to 7 carbon atoms, cyano, nitro, alkylmercapto of 1 to 6 carbon atoms, amino, alkylamino of 1 to 6 carbon atoms, dialkylamino in which each alkyl group is of 1 to 6 carbon atoms, alkanamido of 2 to 7 carbon atoms, halo, trifluoromethyl, or, when taken together, methylene dioxy;
$R_7$ is hydrogen or alkyl of 1 to 6 carbon atoms; and
n is one of the integers 0, 1, 2, 3 or 4;
or a pharmaceutically acceptable salt thereof.

The preferred compounds are those of the formula:

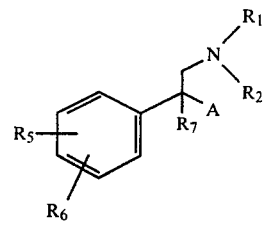

in which
A is defined supra;
$R_1$ is hydrogen or alkyl of 1 to 3 carbon atoms;
$R_2$ is alkyl of 1 to 3 carbon atoms;
$R_5$ is hydrogen, hydroxy, alkoxy of 1 to 3 carbon atoms, chloro, bromo, trifluoromethyl or alkyl of 1 to 3 carbon atoms;
$R_6$ is alkyl of 1 to 3 carbon atoms, alkoxy of 1 to 3 carbon atoms, chloro, bromo, trifluoromethyl or alkanoyloxy of 2 to 3 carbon atoms.
$R_7$ is hydrogen or alkyl of 1 to 3 carbon atoms;
or a pharmaceutically acceptable salt thereof.

The most preferred compounds are those in which $R_5$ and $R_6$ are in meta or para positions and n is 2.

The compounds in which $R_4$ is formyl or alkanoyl of 2 to 7 carbon atoms are not nearly as potent as the corresponding free hydroxy bearing derivatives in the test procedures employed and disclosed herein. However, in long term therapy the acyloxy derivatives will act as pro drugs as the acyl group is removed in vivo either via acid hydrolysis in the stomach or enzymatically.

The pharmaceutically acceptable acid addition salts of the basic compounds of this invention are formed conventionally by reaction of the free base with an equivalent amount of any acid which forms a non-toxic salt. Illustrative acids are either inorganic or organic, including hydrochloric, hydrobromic, fumaric, maleic, succinic, sulfuric, phosphoric, tartaric, acetic, citric, oxalic and similar acids. For parenteral administration, the use of water soluble salts is preferred, although either the free base of the pharmaceutically acceptable salts are applicable for oral or parenteral administration of the antidepressant agents of this invention. The halo substituent representing $R_5$ or $R_6$ is intended to include the chloro, bromo, iodo or fluoro substituents.

The compounds of this invention are produced by reaction of a cycloalkanone or a cycloalkenone with an appropriately substituted (ortho or para) phenylacetonitrile anion following the procedure of Sauvetre et al., Tetrahedron, 34, 2135 (1978) followed by reduction (catalytic hydrogenation, borane reducing agents, LiAlH$_4$, etc.) of the nitrile to a primary amine and alkylation of the amine. In the presence of cyclo aliphatic unsaturation, lithium aluminum hydride is the preferred reducing agent. Subsequent acylation of the α-cycloaliphatic hydroxyl group and any phenolic hydroxyl group present may be effected conventionally with a formylating agent such as formyl fluoride or an alkanoic acid halide or anhydride. Symmetrical N-methylation may be accomplished via a modified Eschweiler-Clarke procedure employing a large excess of water as illustrated by Tilford et al., J.A.C.S. 76, 2431 (1954); alternatively the procedure of Borch and Hassid, J. Org. Chem., 37, 1653 (1972) using sodium cyanoborohydride and formaldehyde may be employed. Non-symmetrical N-alkylation or monoalkylation may be accomplished by stepwise alkylation of the N-trifluoroacetate as illustrated by R. A. W. Johnstone et al., J. Chem. Soc., (C) 2223 (1969). Where R₄ is alkyl it is introduced prior to reduction of the nitrile by conventional O-alkylation.

The intermediate nitriles prepared during the production of the antidepressant agents of this invention represent an additional aspect of the invention. They are depicted by the structural formula:

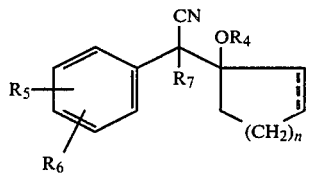

in which the dotted line represents optional unsaturation, and

R₄ is hydrogen or alkyl of 1 to 6 carbon atoms;

R₅ and R₆, one of which may be hydrogen, are ortho or para substituents, independently selected from the group consisting of hydroxyl, alkyl of 1 to 6 carbon atoms, alkoxy of 1 to 6 carbon atoms, aralkoxy of 7 to 9 carbon atoms, alkanoyloxy of 2 to 7 carbon atoms, alkylmercapto of 1 to 6 carbon atoms, halo or trifluoromethyl;

R₇ is hydrogen or alkyl of 1 to 6 carbon atoms; and n is one of the integers 0, 1, 2, 3 or 4.

The intermediate primary amines produced by reduction of the nitrile depicted in the preceding paragraph represent an additional aspect of the invention. They present the following structural formula:

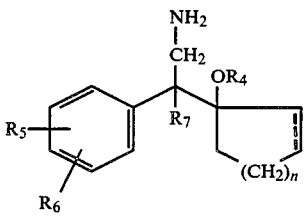

in which the dotted line represents optional unsaturation,

R₄ is hydrogen, or alkyl of 1 to 6 carbon atoms;

R₅ and R₆ are ortho or para substituents independently selected from the group consisting of hydrogen, hydroxyl, alkyl of 1 to 6 carbon atoms, alkoxy of 1 to 6 carbon atoms, aralkoxy of 7 to 9 carbon atoms, alkanoyloxy of 2 to 7 carbon atoms, alkylmercapto of 1 to 6 carbon atoms, halo or trifluoromethyl;

R₇ is hydrogen or alkyl of 1 to 6 carbon atoms; and n is one of the integers 0, 1, 2, 3 or 4.

Symmetrical N,N-dimethylation may be performed readily by reaction of the primary amino derivative with formaldehyde, formic acid in a large excess of water. An intermediate, 3-aza-1-oxaspiro[5.5]undecane, which represents an additional intermediate of this invention is formed during the reaction and is isolatable. It presents the following structural formula:

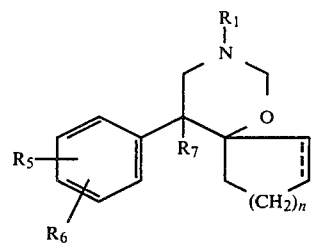

in which the dotted line represents optional unsaturation,

R₁ is methyl;

R₅ and R₆ are ortho or para substituents independently selected from the group consisting of hydrogen, hydroxyl, alkyl of 1 to 6 carbon atoms, alkoxy of 1 to 6 carbon atoms, aralkoxy of 7 to 9 carbon atoms, alkanoyloxy of 2 to 7 carbon atoms, alkylmercapto of 1 to 6 carbon atoms, halo or trifluoromethyl;

R₇ is hydrogen or alkyl of 1 to 6 carbon atoms; and n is one of the integers 0, 1, 2, 3 or 4.

These oxaspiro[5.5]undecane intermediates possess similar activity to the corresponding open-ring tertiary amino end compounds of the invention. For example, the oxazine produced in Example 3 is hereinafter compared, in its properties, with the corresponding dimethylamino end compound of Example 3. The end compound is produced from the corresponding oxazine by prolonged reflux in the presence of aqueous formic acid.

An alternative, and preferred, mode of preparing the compounds of this invention involves the reaction of a cycloalkanone or cycloalkenone with an appropriately substituted phenylacetamide anion following the procedure of Sauvetre et al., ibid., followed by reduction of the amide with lithium aluminum hydride or a borane reducing agent, except in the case of cycloaliphatic unsaturation as discussed, supra, to the corresponding amine. This process is preferred because it is considerably more facile when dealing with meta-substituted or halo-substituted phenylacetamide reactants which pose some problems when proceeding through the acetonitrile intermediate. This route to the desired end products also permits one to readily vary the valued R₁ and R₂ in the initial reactant.

The cyano substituent representing R₅ and/or R₆ is introduced after all reduction steps have been completed by displacement of an R₅-R₆ halo substitution with cuprous cyanide. The amino substituents representing R₅ and/or R₆ are protected throughout the reaction sequence with a protecting group such as 1,1,4,4-tetramethyl-1,4-dichlorosilylethylene which completely blocks the amino nitrogen atom from undesireable reactions. After completion of the reaction sequence, the amino group is deprotected and alkylated or acylated by conventional means to provide a mono- or di-alkylamine or an alkanamido group in each case of 1 to 6 carbo atoms. The nitro substituent representing R₅ and/or R₆ is introduced as an aromatic substituent by diazotization of the aromatic amine followed by treatment with alkali metal nitrite in the presence of copper or by formation of the diazonium tetrafluoroborate and reaction with an alkali metal nitrite, thusly:

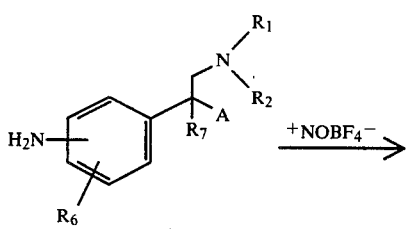

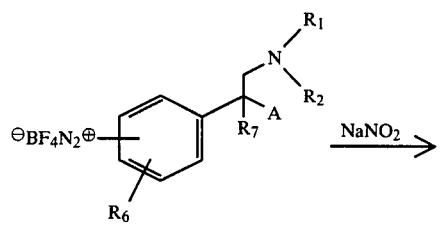

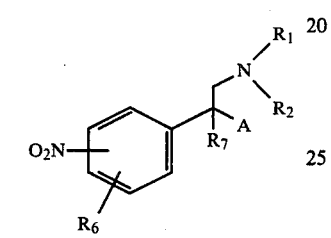

The cyano substituent may be introduced via the diazonium salt with cyprous cyanide in analogous manner.

The intermediate amide represents an additional aspect of this invention and is depicted by the following structural formula:

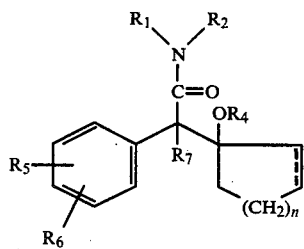

in which the dotted line represents optional unsaturation, $R_1$ is alkyl of 1 to 6 carbon atoms;
$R_2$ is alkyl of 1 to 6 carbon atoms;
$R_4$ is hydrogen or alkyl of 1 to 6 carbon atoms;
$R_5$ and $R_6$, one of which may be hydrogen, are independently, hydroxyl, alkyl of 1 to 6 carbon atoms, alkoxy of 1 to 6 carbon atoms, aralkoxy of 7 to 9 carbon atoms, alkanoyloxy of 2 to 7 carbon atoms, alkylmercapto of 1 to 6 carbon atoms, N-protected amino, halo or trifluoromethyl;
$R_7$ is hydrogen or alkyl of 1 to 6 carbon atoms; and n is one of the integers 0, 1, 2, 3 or 4.

When $R_4$ is alkyl it is introduced prior to reduction. The protecting group employed to prevent reaction at the amino substituent representing $R_5$ and/or $R_6$ is any protecting group that will completely prevent reaction at a primary —NH$_2$ substituent, such as 1,2-[bis-dimethylsilylchloride]ethane.

More indirect routes for synthesis of the antidepressant compounds of this invention involve the reaction of a cycloalkanone or a cycloalkenone with an anion of an appropriately substituted phenylacetic acid, salt, ester, aldehyde or alcohol

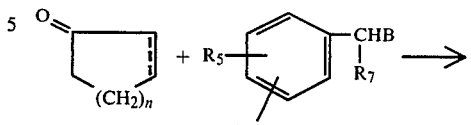

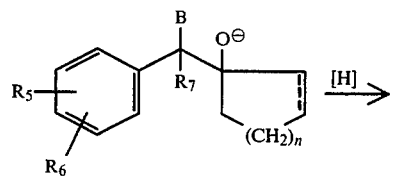

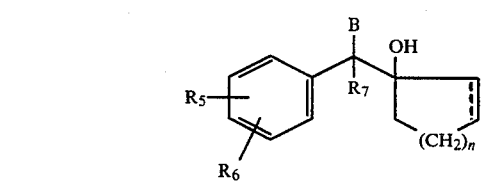

where B represents a carboxyl group or its salt or ester or a —CHO or CH$_2$OH functional group.

The carboxylic acid group may be converted to an acid halide, active ester or anhydride and directly reacted with the desired amine to yield, after reduction of the resulting amide, the end products of this invention. Also, the carboxylic acid group may be reduced with diisobutyl aluminum hydride or lithium aluminum hydride to obtain the corresponding aldehyde. The ester is readily converted to the aldehyde with diisobutyl aluminum hydride or to the alcohol with lithium aluminum hydride. The aldehyde may be condensed with hydroxylamine to afford the oxime —CH=NOH; with ammonium or a primary amine to afford an imine —CH=NR$_1$ or with a primary or secondary amine to afford $$-\overset{\overset{\displaystyle OH}{|}}{CH}-NR_1R_2.$$

The alcohol —CH$_2$OH may be converted to the corresponding nitro derivative by producing an organic sulfonate (mesyl ester) or halide followed by displacement with an inorganic nitrite. Reduction of these intermediates yields the primary amine intermediates or the secondary or tertiary amine end products of this invention. The alcohols may be converted to mesylates or tosylates, reacted with KCN to afford the nitrile, converted to the amide and subjected to a Hoffman rearrangement with bromine or chlorine and an alkali metal hydroxide.

Additional routes to the desired products include the reaction of ammonia or HNR$_1$R$_2$ with

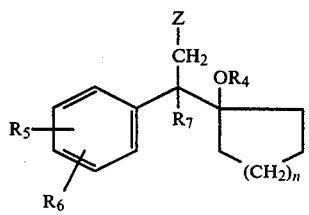

where Z is a leaving group such as a halogen or an organo sulfonyloxy (mesyl, tosyl and the like) group under conventional conditions. If desired, the amine reactant may be initially blocked with a relatively labile acyl group such as trifluoroacetyl to provide a reactant of the formula

prior to reaction with the alkylating reactant employing KOH and a very polar solvent such as dimethylsulfoxide, to provide a tertiary amide from which the acyl group may be readily removed to prepare the compound for non-symmetrical N-alkylation to insert $R_2$. Rather than N-alkylate, one may acylate or react the secondary amine with an aldehyde and subsequently reduce the amide or Schiff base. Similarly, reaction of the amine with an alkylchloroformate affords, upon reduction, an N-methylated amine. LiAlH$_4$ is a good reducing agent for these processes.

Reductive amination of the aldehyde

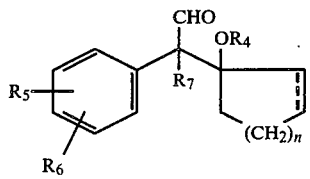

with ammonia, a primary amine or a secondary amine (Leuckart reaction) also yields the desired end products.

During the course of the synthesis of the end compounds of the invention by means of processes identified above, any hydroxy group represented by —OR$_4$, R$_5$ or R$_6$ may be in the free form or in the form of hydroxy protected by a removable protecting group, except of course, that the hydroxy group is not protected in any case where it is intended to participate in a reaction. The protected form is recommended where the hydroxy group may otherwise undergo an undesired reaction. Examples of protecting groups for hydroxy are given in Protective Groups in Organic Chemistry edited by J. F. W. McOmie, Chapters 3 and 4 (pages 95-182), published by Plenum Press (1973), and Protective Groups in Organic Chemistry by T. W. Greene, Chapters 2 and 3 (pages 10 to 113) published by John Wiley and Sons (1981). The protecting group may be removed at a suitable later stage in the synthesis. Similarly any amino or alkylamino group may be in a protected form where appropriate during the course of the synthesis of the end compounds. Protecting groups for amino are described in Chapter 2 (pages 43 to 94) of the McOmie book and Chapter 7 (pages 218 to 286) of the Greene book.

The end products contain either one or two asymmetric centers depending upon the saturated and unsaturated state of the cycloaliphatic ring, respectively. Individual stereoisomeric forms may be obtained or separated by standard procedures. For instance separation of the mixture in the case of an amine or carboxylic acid may be carried out by neutralisation with a suitable optically active compound to form salts which can be separated. Example 33 illustrates the typical resolution of the product of Example 3, Compound A.

The antidepressant activity of the end compounds of this invention was established by demonstrating that they (1) inhibit $^3$H-imipramine binding in brain tissue when tested by a method analogous to that of Raisman et. al., Eur. J. Pharmacol. 61, 373-380 (1980); (2) inhibit synaptosomal uptake of norepinephrine ($^3$H—NE) and serotonin ($^{14}$C-5-HT) following the test procedure of Wood et. al., J. Neurochem. 37, 795-797 (1981); and antagonize reserpine induced hypothermia when tested in accordance with the procedure of Askew, Life Sci. 1, 725-730 (1963).

The results of these procedures affirmed the antidepressant activity of the end compounds of this invention in aggreement with the most widely accepted theory of antidepressant activity and in correlation of activity with known tricyclic antidepressants. In at least two instances, namely, with the dimethylamino product of Example 3, and 4-chloro product in Example 11, the undesirable attribute of classical antidepressants observed as an anticholinergic property which is reflected by the inhibition of binding of the muscarinic receptor ligand, 3H-quinuclidinyl benzilate (QNB), and in the inhibition of carbachol-stimulated contraction of the guinea-pig ileum, is missing. Also missing is the attribute of classical antidepressants observed as an antihistaminic property which is reflected by the inhibition of the H$_1$ histamine receptor ligand, 3H-pyrilamine, and in the inhibition of histamine-stimulated contraction of the guinea-pig ileum.

As representative examples of the activity profile of the end compounds of this invention, the following data for testing of the dimethylamino product of Example 3, hereinafter Compound A, its oxazine variant, hereinafter Compound B, the 4-chloro product of Example 11, hereinafter referred to as Compound C, the 4-bromo product of Example 15, hereinafter referred to as Compound D, the 3-chloro product of Example 17, hereinafter referred to as Compound E, the 3-bromo product of Example 16, hereinafter referred to as Compound F, and the 3,4-dichloro product of Example 19, hereinafter referred to as Compound G, are presented as follows:

Inhibition of $^3$H-imipramine binding:

Compound A (HCl Salt) exhibited an inhibition constant (K$_i$) vs. $^3$H-imipramine of 90 nM, making it a fairly potent ligand at this receptor site. Compound B was somewhat less potent, with a K$_i$ of 350 nM. Compound C was virtually equipotent with Compound A, exhibiting a K$_i$ vs. $^3$H-imipramine of 100 nM. While not as potent as imipramine (K$_i$=1.7 nM), these values fall in the range of desmethylimipramine (DMI) (K$_i$=130 nM) and other tricyclic antidepressants. Atypical antidepressants (non-tricyclic) which have been tested, exhibit K$_i$'s greater than 5000 nM in this assay. Compounds D, E, F and G exhibited inhibition constants of 62, 130, 52 and 37, respectively. Compounds A through G, representative of the other compounds of this invention, are thus comparable to known tricyclic antidepressants in this test.

Inhibition of synaptosomal NE and 5-HT uptake:

Results of the inhibition of NE and 5-HT synaptosomal uptake, expressed as the inhibitory concentration at which the rate of uptake was reduced to 50 percent (IC$_{50}$), are presented in the table below, where they are compared with the values for imipramine, DMI and amitriptyline:

| Compound | IC$_{50}$ ($\mu$M) | |
|---|---|---|
| | NE | 5-HT |
| Imipramine | 0.26 | 0.12 |
| DMI | 0.15 | 3.0 |
| Amitriptyline | 0.50 | 0.60 |
| Compound A | 0.64 | 0.21 |
| Compound B | 4.7 | 2.9 |
| Compound C | 0.33 | 0.25 |
| Compound D | 0.21 | 0.11 |
| Compound E | 0.16 | 0.32 |
| Compound F | 0.11 | 0.23 |
| Compound G | 0.07 | 0.08 |

These results show that Compounds A and C to G are approximately equipotent to imipramine in NE and 5-HT uptake inhibition. Again, Compound B is somewhat less potent.

Inhibition of $^3$H-QNB binding:

In the QNB receptor binding assay, the Compounds A and C-G exhibited an IC$_{50}$ greater than 10$^{-5}$ molar and were therefore essentially inactive. Imipramine and DMI exhibit K$_i$'s of 37 nM and 50 nM, respectively. These results suggest that, unlike the tricyclic antidepressants, Compounds A and C-G would have no muscarinic anticholinergic actions.

Inhibition of Carbachol-stimulated contraction of guinea-pig ileum:

While imipramine at 1 $\mu$M exhibits a K$_B$ of approximately 100 nM against carbachol-stimulated contraction of the guinea-pig ileum, Compound A was inactive at 1 $\mu$M. This result supports the suggestion of a lack of muscarinic anticholinergic action of Compound A.

Inhibition of $^3$H-pyrilamine binding:

While DMI exhibits a K$_i$ versus $^3$H-pyrilamine binding of 124 nM, Compound A was inactive. Compounds D-G exhibited an IC$_{50}$ greater than 10$^{-5}$ molar. These results suggest that, unlike tricyclic antidepressants, Compounds A and D-G have no antihistaminic property.

Inhibition of histamine-stimulated contraction of the guinea-pig ileum:

Imipramine at 1 $\mu$M inhibits the histamine-stimulated contraction of the guinea-pig ileum with an approximate K$_B$ of 8 nM. Compound A, in contrast, had no effect in this test at a concentration of 1 $\mu$M. This result supports the notion that Compound A has no antihistaminic action.

Antagonism of reserpine-induced hypothermia:

The minimum effective dose (M.E.D.) of compounds A through G established in antagonism of reserpine-induced hypothermia in mice (n=8 per group) in relation to desmethylimipramine (DMI) were:

| Compound | Dose, mg/kg, i.p. |
|---|---|
| DMI | 0.4 (and p.o.) |
| A | 10.0 |
| B | 30.0 |
| C | 10.0 |
| D | 3.0 |
| E | 1.0 |
| F | 1.0 |
| G | 3.0 |

All mice received 5 mg/kg reserpine s.c. 18 h prior to test compound.

DMI, and Compounds A to G, are of approximately equal efficacy in the reversal of reserpine-induced hypothermia. Compound B was less potent than Compound A, Compound C was approximately equipotent with Compound A, Compounds D and G were approximately three times as potent as Compound A, and Compounds E and F were approximately ten times as potent as Compound A in the study.

Hence, the end compounds of this invention are useful in the treatment of depression, for which purpose they may be administered orally or parenterally in an amount sufficient to alleviate the symptoms of depression. The actual amount of antidepressant agent to be used will vary with the severity and nature of the depressed state, the animal being treated and the level of relief sought. In the human, an oral dose of from about 2 to about 50 milligrams, administered as needed represents appropriate posology. Intramuscular administration of from about 1 to about 25 milligrams provides a dosage comparable to that specified for oral administration. As with other antidepressants, therapy should be initiated with lower dosages and increased until the desired symptomatic relief is obtained.

Pharmaceutical compositions containing the antidepressant compounds of this invention represent an additional aspect of this invention. The active ingredient can be compounded into any of the usual oral dosage forms including tablets, capsules and liquid preparations such as elixirs and suspensions containing various colouring, flavouring, stabilizing and flavour masking substances. For compounding oral dosage forms, the active ingredient can be mixed with various conventional tabletting materials such as starch, calcium carbonate, lactose, sucrose and dicalcium phosphate to aid the tabletting or capsulating process. Magnesium stearate, as an additive, provides a useful lubricant function when desired.

The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example, packeted powders or vials or ampoules. The unit dosage form can be a capsule, cachet or tablet itself, or it can be the appropriate number of any of these in package form. The quantity of the active ingredient in a unit dose of composition may be varied or adjusted from 2 mg. or less to 50 mg. or more, according to the particular need and the activity of the active ingredient.

The following examples illustrate the preparative technique employed in production of the compounds of the invention.

EXAMPLE 1

1-[Cyano(p-methoxyphenyl)methyl]cyclohexanol p-Methoxyphenylacetonitrile (50 gm, 0.3 mole) was added to dry tetrahydrofuran (250 ml) and the solution cooled to −70° C. under nitrogen. n-Butyl lithium in hexane (210 ml, 0.3 mole) was added dropwise, with stirring. The temperature was maintained below −50° C. and a yellow precipitate appeared. After the addition was complete, the reaction mixture was maintained below −50° C. for 30 minutes and cyclohexanone (35 ml, 0.3 mole) was added. After a further 45 minutes below −50° C. the temperature was allowed to rise to 0° C. and a saturated ammonium chloride solution was added. The layers were separated and the aqueous layer extracted with diethyl ether. The combined organic solution was washed with brine, dried over magnesium sulphate and evaporated. The product crystallized (25.2 gm, m.p. 125°–127° C.).

Mass Spectral Analysis: Molecular weight 245 [(M+1)+ by C.I.M.S.]

N.M.R. Analysis: δ 7.32, 6.95; (4H quartet, p-substituted aromatic) 3.8 (3H singlet, O—CH$_3$); 3.76 (1H, singlet, C$\underline{H}$—CN); 1.56 (10H, multiplet, aliphatic cyclohexyl)ppm.

EXAMPLE 2

1-[2-amino-1-(p-methoxyphenyl)ethyl]cyclohexanol

1-[cyano(p-methoxyphenyl)methyl]cyclohexanol (12 g, 0.05 mole) was dissolved on warming in a mixture of ammonia-ethanol (20% v/v, 250 ml) and hydrogenated in a Parr apparatus over 5% rhodium on alumina (2.8 gm). The catalyst was filtered, washed well with ethanol and the combined filtrate evaporated and dried under vacuum yielding an oil (12 gm).

Mass Spectral Analysis: Molecular weight 249 (M+1)+ by C.I.M.S.

Thin Layer Chromatography: single spot, ninhydrin positive [chloroform-methanol-acetic acid (80:10:10 v/v)].

EXAMPLE 3

5-(4-methoxyphenyl)-3-methyl-3-aza-1-oxaspiro(5.5)-undecane and 1-[2-dimethyl-amino)-1-(4-methoxyphenyl)ethyl]cyclohexanol 1-[2-amino-1-(p-methoxyphenyl)ethyl]cyclohexanol (12 gm; 0.048 mole) was treated with a mixture of formaldehyde (11 ml), formic acid (14.5 ml, 88%) and water (125 ml) and heated at 100° C. for five hours. The reaction mixture was cooled and extracted with ethyl acetate. This extract was discarded. The aqueous residue was cooled in ice, rendered basic by the addition of solid potassium hydroxide, saturated with sodium chloride and thrice extracted with ethyl acetate. The extract was washed with brine, dried over anhydrous potassium carbonate and evaporated to an oily residue (8 gm). This mixture of products was chromatographed on 1 kg of Mallinckrodt Silicar CC7 silica gel and the progress of the chromatography was monitored by thin layer chromatography using a system comprising ethanol:2N ammonia:ethyl acetate:cyclohexane 45:8:100:100 (v/v). Fractions containing the desired products were combined and the hydrochloride salts prepared using 4-N-isopropanolic HCl. The yields of the free bases were 1.4 gm (spiro compound) and 4.6 gm (dimethylamine) respectively.

COMPOUND B 5-(4-methoxyphenyl)-3-methyl-3-aza-1-oxaspiro(5.5) undecane

Melting Point: 242°–244° C.

Mass Spectral Analysis: Molecular weight 275 (M+1)+ by C.I.M.S.

N.M.R. Analysis: δ 7.22, 6.96 (4H quartet, p-substituted aromatic) 4.78 (2H quartet, O—CH$_2$—NCH$_3$) 3.8 (4H, O—CH$_3$, CH—CH$_2$—NCH$_3$) 3.3 (2H, multiplet C$\underline{H}$—CH$_2$—NC$\underline{H}$$_3$) 2.8 (3H, NCH$_3$) 0.9–1.8 (10H, broad multiplet, aliphatic cyclohexyl)ppm.

COMPOUND A

1-[(2-dimethylamino)-1-(4-methoxyphenyl)ethyl]cyclohexanol

The hydrochloride: m.p. 215°–217° C.

Mass Spectral Analysis: Molecular weight 279 (M+1)+ by C.I.M.S. (free base)

N.M.R. Analysis: δ 7.32, 6.98 (4H quartet, p-substituted aromatic) 3.78 (3$\underline{H}$, O—CH$_3$) 3.64 (2$\underline{H}$, multiplet C$\underline{H}$$_2$N(CH$_3$)$_2$) 3.06 (1H, multiplet C$\underline{H}$—CH$_2$(NCH$_3$)$_2$) 2.74 (6H, N(CH$_3$)$_2$) 1.38 (10H, broad multiplet, alphatic cyclohexyl)ppm.

EXAMPLE 4

1-[1-(4-methoxyphenyl)-2-dimethylaminoethyl]cyclohexene 8.0 grams (0.029 moles) of 1-[1-(4-methoxyphenyl)-2-dimethylaminoethyl]cyclohexanol was dissolved in 300 ml of 2.0N aqueous hydrochloric acid and heated at reflux for 18 hours. It was allowed to cool, neutralized with 15% aqueous sodium hydroxide and extracted with chloroform. The chloroform extract was dried over sodium sulfate, filtered, and concentrated in vacuo to yield 7.0 grams of solid. This material was converted to the hydrochloride salt by treatment with 5N isopropanolic HCl and recrystallized a second time from isopropanol to yield 2.0 grams of the title compound as a white solid hydrochloride salt, m.p. 187°–189° C.

Analysis for: C$_{17}$H$_{26}$ONCl; Calculated: C, 69.23; H, 8.91; N, 4.75; Found: C, 69.39; H, 8.95; N, 4.95.

EXAMPLE 5

1-[(α-Aminomethyl)benzyl]-cyclohexanol

Phenylacetonitrile (10 g, 0.08 mole) was added to dry THF (100 ml) and the solution cooled to −70° C. under nitrogen. n-Butyllithium in hexane (64 ml, 0.1 mole) was added dropwise, the temperature being maintained below −40° C. and a yellow precipitate appeared. After addition the reaction mixture was maintained near −70° C. for 30 minutes and cyclohexanone (10 g, 0.1 mole) was added. After a further 45 minutes at −70° C. the temperature was allowed to rise to 0° C. and saturated ammonium chloride solution was added. The layers were separated and the aqueous layer extracted with diethyl ether. The combined organic solution was washed with brine, dried over magnesium sulphate and evaporated. The product, 1-[α-cyanobenzyl]-cyclohexanol, crystallized (4.93 g, m.p. 100°–102° C.).

Mass Spectral Analysis: Molecular weight 215 (M+).

N.M.R. Analysis: δ 7.4 (5H singlet, aromatic 3.8 (1H, singlet, C$\underline{H}$—CN) 1.6 (10H, multiplet aliphatic cyclohexyl) ppm.

A solution of 1-(α-cyanobenzyl)cyclohexanol (3.43 g, 0.02 mole) in a mixture of methanol and ammonia (9:1 v/v, 60 ml) was hydrogenated in a Parr apparatus over 5% rhodium on alumina (2 g). The catalyst was filtered and the filtrate evaporated. The residue was dissolved in ethyl acetate, washed with brine, dried over magnesium sulfate and evaporated. The hydrochloride m.p. 220°–222° (1.2 g) crystallized from diethyl ether-acetone.

Analysis for: $C_{14}H_{21}NO.HCl$; Calculated: C, 64.29; H, 8.67; N, 5.47%; Found: C, 65.74; H, 8.51; N, 5.56%.

N.M.R. Analysis (DMSO) δ 7.73 (5H singlet, aromatic) 3.46 (2H multiplet $CH_2$—$NH_2$), 3.0 (1H multiplet C$\underline{H}$—$CH_2NH_2$) 0.9–1.7 (10$\overline{H}$ multiplet-aliphatic cyclohexyl) ppm.

Mass Spectral Analysis by Chemical Ionization: 220 $(M+H)^+$ (Mol. Wt. 219) (free base).

EXAMPLE 6

1-(α-[(Dimethylamino)methyl]benzyl)-cyclohexanol

1-[α-(aminomethyl)benzyl]cyclohexanol (1.38 g, 0.006 mole) was dissolved in a mixture of formaldehyde (2 ml) formic acid (2.6 ml) and water (25 ml), and refluxed at 95° C. for 18 hours. The reaction mixture was cooled, basified with solid KOH and extracted with methylene chloride. The extract was washed with brine, dried over magnesium sulphate and evaporated. The hydrochloride (m.p. 225°–227° C.) was prepared using 3N-isopropanolic HCl. Yield 589 mg.

Analysis for: $C_{16}H_{25}NO.HCl$; Calculated: C, 67.36; H, 9.12; N, 4.88%; Found: C, 67.7; H, 9.23; N, 4.93%.

Mass Spectral Analysis: Molecular weight 247 ($M^+$, free base).

N.M.R. analysis: (DMSO) δ 7.4 (5H singlet, aromatic), 3.68 (2H, multiplet $CH_2$—N $(CH_3)_2$, 3.18 (1H, multiplet C$\underline{H}$—$CH_2N(CH_3)_2$ 2.68 (6H, $N(CH_3)_2$; 0.9–1.7 (10$\overline{H}$ multiplet aliphatic cyclohexyl) ppm.

EXAMPLE 7

1-(α-[(Methylamino)methyl]benzyl)cyclohexanol

1-[α-(aminomethyl)benzyl]cyclohexanol (1.59 g., 0.007 mole) was dissolved in diethyl ether (10 ml.) and cooled to 5° C. Trifluoroacetic anhydride (2 g) was added and the mixture stirred at 0° C. for 30 minutes. The mixture was neutralized using saturated sodium bicarbonate solution and the layers separated. The organic layer was washed with brine, dried over magnesium sulphate and evaporated. A crystalline trifluoroacetamide m.p. 78°–80° C. was obtained (975 mg.).

The trifluoroacetamide (975 mg.) was dissolved in dry acetone (20 ml.) and treated with methyl iodide (2 g.). The solution was warmed to reflux temperature and dry powdered potassium hydroxide (1 g.) added, followed by excess methyl iodide. The mixture was refluxed for five minutes, then cooled and the acetone evaporated. Water (20 ml.) was added and the mixture refluxed for 15 minutes. It was cooled and extracted with ethyl acetate. The extract was washed with water and brine, dried over magnesium sulfate and evaporated to a crystalline product m.p. 92°–94° C. This was converted to the hydrochloride using 3N-isopropanolic HCl. Yield 235 mg., m.p. 208°–210° C.

N.M.R. Analysis (CHCl$_3$), δ 7.3 (7H, aromatic, $\underline{H}$Cl and N$\underline{H}$.CH$_3$); 3.9 (1H multiplet C$\underline{H}$—$CH_2NH_2$); $\overline{3.25}$ (2H multiplet $CH_2$—$NH_2$); 2.6 (3$\overline{H}$ singlet NH—C$\underline{H}_3$); 0.8–1.9 (10H multiplet, aliphatic cyclohexyl) ppm.

Mass Spectral Analysis: Molecular weight by chemical ionization/M.S. 233 (M+1 at 234, free base).

EXAMPLE 8

1-(α-[(Dimethylamino)methyl]benzyl)cyclohexanol acetate 1-(α-[(Dimethylamino)methyl]benzyl)cyclohexanol, (0.5 g., 0.0025 mole) was treated with acetic anhydride (1 ml.) and pyridine (3 ml.) and the mixture stood at room temperature overnight. The reaction mixture was poured into water, basified with solid KOH and extracted with ethyl acetate. The extract was washed with water and brine, dried over magnesium sulphate and evaporated to an oil. After azetropic distillation with toluene to remove traces of pyridine, the oil was treated with 3N isopropanolic HCl and crystalline hydrochloride as the title compound was obtained (70 mg.) m.p. 163°–165° C.

NMR Analysis: (CHCl$_3$) δ 7.35 (5H singlet, aromatic); 4.2 (1H multiplet CHCH$_2$N(CH$_3$)$_2$; 3.6 (2H multiplet CH$_2$—N(CH$_3$)$_2$); 2.$\overline{65}$ (6H singlet, N(CH$_3$)$_2$); 2.1 (3H sing$\overline{let}$, —O—C—C$\underline{H}_3$); 0.9–1.7 (10H multiplet, aliphatic cyclohexyl) ppm.

Mass Spectral Analysis: Molecular weight 289 ($M^+$, free base).

EXAMPLE 9

1-[cyano(p-chlorophenyl)methyl]cyclohexanol

By replacing the p-methoxyphenyl acetonitrile in Example 1 by a molar equivalent amount of p-chlorophenyl acetonitrile, there was obtained 1-cyano(p-chlorophenyl)methyl cyclohexanol (13.7 g.) m.p. 115°–117°.

Mass Spectral Analysis: Molecular weight 249 $(M+1)^+$ by C.I.M.S.

EXAMPLE 10

1-[2-amino-1-(4-chlorophenyl)ethyl]cyclohexanol

Lithium aluminum hydride (3.5 g.) was suspended in ice cold tetrahydrofuran (125 ml.) and concentrated sulphuric acid (2.5 ml.) added cautiously, with stirring. After one hour, 1-[cyano(p-chlorophenyl)methyl]cyclohexanol (15 g., 0.06 mole) was dissolved in tetrahydrofuran (100 ml.) and added rapidly dropwise with vigorous stirring and cooling. After a further two hours, a tetrahydrofuran-water mixture (1:1; 30 ml.) was added followed by 10% sodium hydroxide solution (50 ml.). The tetrahydrofuran was decanted and the residue washed well with diethyl ether and ethylacetate. The combined organic solution was dried over anhydrous potassium carbonate and evaporated to an oil (12 g.)

Mass Spectral Analysis: Molecular weight 253 $(M+1)^+$ by C.I.M.S.

EXAMPLE 11

1-[1-(4-chlorophenyl)-2-(dimethylamino)ethyl]cyclohexanol

1-[2-amino-1-(4-chlorophenyl)ethyl]cyclohexanol (12 g., 0.04 mole) was treated with a mixture of formaldehyde (13.7 ml.) formic acid (18.1 ml.) and water (160 ml.) and refluxed at 100° C. for four hours. The reaction mixture was cooled extracted well with ethyl acetate and the extract discarded. The aqueous residue was cooled in ice and rendered basic by the addition of solid potassium hydroxide, saturated with sodium chloride and thrice extracted with ethyl acetate. The extract was washed with brine, dried over anhydrous potassium carbonate and evaporated. A crystalline solid (3 g.) was filtered. It was converted to the hydrochloride salt using 4N-isopropanolic HCl; yielding 4.7 g., m.p. 241°–243° C.

Mass Spectral Analysis: Molecular Weight 281 (M+1)+ by C.I.M.S.

NMR Analysis: δ 7.35 (4H singlet characteristic of 4-chloro substitution) 3.65 (2H multiplet, $CH_2$—$CHN(CH_3)_2$), 3.0 (1H multiplet $C\overline{H}_2C\underline{H}N(CH_3)_2$ 1.4 (10H multiplet, aliphatic cyclohexyl) ppm.

EXAMPLE 12

1-[1-(4-methoxyphenyl)-2-(methylamino)ethyl]cyclohexanol

By replacing 1-[α-(aminomethyl)benzyl]cyclohexanol with a molar equivalent amount of 1-[2-amino-1-(p-methoxyphenyl)ethyl]cyclohexanol in Example 7, 1-[1-(4-methoxyphenyl)-2-methylamino)ethyl]cyclohexanol hydrochloride (m.p. 164°–166° C.) was obtained.

Mass Spectral Analysis: Molecular Weight 263 (M+1)+ by C.I.M.S.

NMR Analysis: δ 7.28, 6.92 (4H quartet, p-substituted aromatic) 3.76 (3H singlet, OMe) 3.4 (2H multiplet, $CH_2$—$CHNCH_3)_2$ 2.9 (1H multiplet, $CH_2\overline{C}\underline{H}N(CH_3)_2$) 2.54 (3H, $NCH_3$) 1.4 (10H broad multiplet, aliphatic cyclohexyl) ppm.

EXAMPLE 13

4-bromo-N,N-dimethylbenzene acetamide

Para-bromophenylacetic acid (50 g., 0.233 mole) was dissolved in methylene chloride (500 ml) and treated with oxalyl chloride (23.3 ml., 0.27 mole) and D.M.F. (0.5 ml) at room temperature. The mixture was stirred for four hours until gas evolution ceased. The solvent was evaporated and the residue dried under vacuum to remove excess oxalyl chloride. The residue was dissolved in methylene chloride (300 ml) and treated with an excess of gaseous dimethylamine. The mixture was stirred overnight and the solvent evaporated. The residue was redissolved in methylene chloride and the solution washed with saturated sodium bicarbonate solution, N-hydrochloric acid, water, brine, dried over magnesium sulphate and evaporated. The buff-colored crystals were filtered with hexane and air-dried. Yield 51.2 g., m.p. 73°–76° C.

Analysis for: $C_{10}H_{12}NOBr$; Calculated: C, 49.59; H, 4.96; N, 5.79; Found: C, 48.98; H, 5.14; N, 5.77.

NMR Analysis (CHCl₃): δ 7.55 (4H quartet, aromatic) 3.65 (2H singlet) 2.95 (6H singlet, $N(CH_3)_2$) ppm.

EXAMPLE 14

1-[(4-bromophenyl)[(dimethylamino)carbonyl]methyl]cyclohexanol 4-bromo-N,N-dimethylbenzene acetamide (15 g., 0.06 mole) was added to dry T.H.F. (250 ml) and the solution cooled to −78° C. under nitrogen. Straight chain butyl lithium in hexane (43.3 ml, 0.06 mole) was added dropwise, the temperature being maintained below −70° C. throughout. An orange coloured precipitate formed. After addition, the reaction mixture was maintained near −70° C. for 20 minutes and cyclohexanone (7.5 ml, 0.07 mole) was added. After a further 50 minutes at −78° C. the reaction mixture was poured into stirring saturated ammonium chloride solution. The layers were separated and the aqueous layer extracted with diethyl ether. The combined organic solution was washed with brine, dried over magnesium sulfate and evaporated. The product crystallised and was filtered with isopropanol (9.8 g., m.p. 140°–144° C.).

Analysis for: $C_{16}H_{22}NO_2Br$; Calculated: C, 56.47; H, 6.47; N, 4.12; Found: C, 57.22; H, 6.66; N, 4.21.

NMR Analysis (CHCl₃) δ 7.35 (4H, aromatic) 3.63 (1H singlet CH—$CON(CH_3)_2$) 2.95 (6H singlet, N—$(CH_3)_2$); 1.45 (10H multiplet, aliphatic cyclohexyl) ppm.

EXAMPLE 15

1-[1-(4-bromophenyl)-2-(dimethylamino)ethyl]cyclohexanol

Lithium aluminum hydride (0.7 g.) was suspended in dry THF (25 ml) cooled to 0° C. and concentrated sulfuric acid (0.5 ml) cautiously added in an in situ preparation of aluminum hydride. The mixture was stirred for one hour at 0° C. and the amide, 1-[(4-bromophenyl)[dimethylaminocarbonyl]methyl]cyclohexanol (4 g., 0.012 mole) was dissolved in THF (35 ml) and added rapidly dropwise. The reaction mixture was stirred at 0° C. for one hour. A THF-water mixture (1:1 v/v 6 ml) was added slowly followed by 10% sodium hydroxide (10 ml). The mixture was filtered and the residue washed well with ethyl acetate. The combined filtrate was dried over anhydrous potassium carbonate and evaporated to an oil (3.5 g) which was converted to the hydrochloride salt using 4N isopropanolic HCl.

Analysis for: $C_{16}H_{24}NOBr.HCl$; Calculated: C, 52.97; H, 6,9; N, 3.86; Found: C, 52.71; H, 6.63; N, 3.71.

NMR Analysis: (DMSO): δ 7.4 (4H, aromatic) 3.55 (2H doublet CH—$CH_2N(CH_3)_2$); 3.05 (1H, triplet, CH—$CH_2N(CH_3)_2$); 2.63 (6H singlet, N—$(CH_3)_2$) 1.30 (10H multiplet, aliphatic cyclohexyl) ppm.

EXAMPLE 16

1-[1-(3-bromophenyl)-2-(dimethylamino)ethyl]cyclohexanol

By replacing p-bromophenyl acetic acid with a molar equivalent amount of m-bromophenyl acetic acid in Example 13, and following procedures described in Examples 14 and 15, 1-[1-(3-bromophenyl)-2-(dimethylamino)ethyl]cyclohexanol was obtained as the hydrochloride, m.p. 198°–201° C.

Analysis for: $C_{16}H_{24}NOBr.HCl$; Calculated: C, 52.97; H, 6.90; N, 3.86; Found: C, 52.84; H, 6.92; N, 3.99.

EXAMPLE 17

1-[1-(3-chlorophenyl)-2-(dimethylamino)ethyl]cyclohexanol

By replacing p-bromophenyl acetic acid with a molar equivalent amount of m-chlorophenylacetic acid in Example 13, and following procedures described in Examples 14 and 15, 1-[1-(3-chlorophenyl)-2-(dimethylamino)ethyl]cyclohexanol was obtained as the hydrochloride, m.p. 214°–216° C.

Analysis for: $C_{16}H_{24}NOCl.HCl$; Calculated: C, 60.38; H, 7.86; N, 4.4; Found: C, 60.07; H, 7.79; N, 3.93.

EXAMPLE 18

1-[1-(2-Chlorophenyl)-2-(dimethylamino)ethyl]cyclohexanol

By replacing p-bromophenyl acetic acid with a molar equivalent amount of o-chlorophenylacetic acid in Example 13, and following procedures described in Examples 14 and 15, 1-[1-(2-chlorophenyl)-2-(dimethylamino)ethyl]cyclohexanol was obtained as the hydrochloride, m.p. 205°–206° C.

Analysis for: $C_{16}H_{24}NOCl.HCl$; Calculated: C, 60.38; H, 7.86; N, 4.4; Found: C, 60.45; H, 7.71; N, 4.79.

EXAMPLE 19

1-[1-(3,4-dichlorophenyl)-2-(dimethylamino)ethyl]cyclohexanol

By replacing p-bromophenyl acetic acid with a molar equivalent amount of 3,4-dichlorophenylacetic acid in Example 13, and following procedures described in Examples 14 and 15, 1-[1-(3,4-dichlorophenyl-2-(dimethylamino)ethyl]cyclohexanol was obtained as the hydrochloride, m.p. 241°–244° C.

Analysis for: $C_{16}H_{23}NOCl_2.HCl$; Calculated: C, 54.47; H, 6.81; N, 3.97; Found: C, 54.8; H, 6.83; N, 3.99.

EXAMPLE 20

1-[1-(3,4-dichlorophenyl-2-(dimethylamino)ethyl]cyclohexanol

The product of the preceding example is similarly produced by the following procedure:

Lithium diisopropylamide was prepared by dissolving di-isopropylamine (69 ml) in THF (500 ml) followed by the addition of n-butyllithium (325 ml). After 10 minutes stirring, the straw colored liquid was cooled to −78° C. and a solution of the 3,4-dichloro-N,N-dimethylbenzeneacetamide (110.9 g, crude) was dissolved in 300 ml THF and added slowly. A dark red slurry was obtained. The mixture was stirred for a further 20 minutes and cyclohexanone (55.7 ml) was added. After 60 minutes at −78° C. the reaction mixture was poured into a saturated solution of ammonium chloride. The aqueous layer was extracted with diethyl ether and the combined organic solution was washed with brine, dried over $K_2CO_3$ and evaporated. The product, 1-[(3,4-dichlorophenyl)(dimethylaminocarbonyl)methyl]cyclohexanol, crystallized and was filtered. The crystals were washed with isopropanol and with petroleum ether and air dried. Yield: 73.6 g., m.p. 118°–120° C.

To an ice cold solution of Borane THF complex (152 ml, 152 mmole) was added a solution of 1-[(3,4-dichlorophenyl)(dimethylaminocarbonyl)methyl]cyclohexanol (30 g, 90 mmole) in THF. The mixture was refluxed for 2 hours and cooled again in an ice bath. 2N HCl (23 ml) was added and the mixture refluxed for 1.5 hours. It was cooled overnight. The reaction mixture was basified to pH 14 with solid potassium hydroxide and the layers were separated. The organic layer was washed with brine, dried over magnesium sulfate and evaporated to a solid. This was filtered and washed with diethyl ether and air dried. Yield: 15.4 g.; m.p. 128°–130° C.

This product was converted to the hydrochloride which was identical with the product in Example 19.

EXAMPLE 21

1-[2-(dimethylamino)-1-(3-methoxyphenyl)ethyl]cyclohexanol

By replacing p-bromophenyl acetic acid with a molar equivalent amount of m-methoxyphenyl acetic acid in Example 13, and following procedures described in Examples 14 and 15, 1-[2-(dimethylamino)-1-(3-methoxyphenyl)ethyl]cyclohexanol was obtained as the hydrochloride, m.p. 166°–168° C.

Analysis for: $C_{16}H_{25}NO_2.HCl$; Calculated: C, 64.11; H, 8.68; N, 4.67; Found: C, 63.12; H, 8.54; N, 4.46.

EXAMPLE 22

1-[1-(3,4-dimethoxyphenyl)-2-(dimethylamino)ethyl]cyclohexanol

By replacing p-bromophenyl acetic acid with a molar equivalent amount of 3,4-dimethoxyphenyl acetic acid in Example 13, and following procedures described in Examples 14 and 15, 1-[1-(3,4-dimethoxyphenyl)-2-(dimethylamino)ethyl]cyclohexanol was obtained as the hydrochloride.

Analysis for: $C_{18}H_{29}NO_3.HCl$; Calculated: C, 62.88; H, 8.74; N, 4.08; Found: C, 62.42; H, 8.56; N, 3.98.

EXAMPLE 23

1-[2-(dimethylamino)-1-(4-trifluoromethylphenyl)ethyl]cyclohexanol

By replacing p-bromophenyl acetic acid with a molar equivalent amount of p-trifluoromethylphenyl acetic acid in Example 13, and following procedures described in Examples 14 and 15, 1-[2-(dimethylamino)-1-(4-trifluoromethylphenyl)ethyl]cyclohexanol was obtained as the hydrochloride, m.p. 238°–240° C.

Analysis for: $C_{17}H_{25}NOF_3.HCl$; Calculated: C, 58.03; H, 7.16; N, 3.98; Found: C, 58.47; H, 7.16; N, 4.07.

EXAMPLE 24

1-[2-(dimethylamino)-1-(3-trifluoromethylphenyl)ethyl]cyclohexanol

By replacing p-bromophenyl acetic acid with a molar equivalent amount of m-trifluoromethylphenyl acetic acid in Example 13, and following procedures described in Examples 14 and 15, 1-[2-(dimethylamino)-1-(3-trifluoromethylphenyl)ethyl]cyclohexanol was produced as the hydrochloride, m.p. 194°–196° C.

Analysis for: $C_{17}H_{25}NOF_3.HCl$; Calculated: C, 58.03; H, 7.16; N, 3.98; Found: C, 58.31; H, 7.09; N, 4.09.

EXAMPLE 25

1-[2-(dimethylamino)-1-(4-methylphenyl)ethyl]cyclohexanol

By replacing p-bromophenyl acetic acid with a molar equivalent amount of p-methylphenyl acetic acid in Example 13, and following procedures described in Examples 14 and 15, 1-[2-(dimethylamino)-1-(4-methylphenyl)ethyl]cyclohexanol was produced as the hydrochloride.

Analysis for: $C_{17}H_{17}NO.HCl$; Calculated: C, 68.54; H, 9.17; N, 4.70; Found: C, 68.37; H, 9.31; N, 4.83.

EXAMPLE 26

1-[2-(dimethylamino)-1-(4-hydroxyphenyl)ethyl]cyclohexanol

By replacing p-bromophenyl acetic acid with a molar equivalent amount of p-benzyloxyphenyl acetic acid in Example 13, and following the procedures described in Examples 14 and 15, 1-[1-(4-benzyloxyphenyl)-2-(dimethylamino)ethyl]cyclohexanol was obtained.

Hydrogenolysis of this product to remove the benzyl protecting group from the 4-hydroxyphenyl moiety was accomplished by dissolving 1.0 grams of the product in 100 ml. ethanol. One gram, 10% Pd/C was introduced followed by cyclohexa-1,4-dienone (5 ml.). The mixture was stirred for ninety minutes at ambient temperature. The catalyst was removed by filtration and the solvent removed by evaporation to yield 800 mg. of solid. This solid 4-hydroxyphenyl product was converted to its fumarate salt via an acetone-ethanol solution, m.p. 140°–142° C.

Analysis for: $C_{16}H_{25}NO_2 \cdot C_4H_4O_4$; Calculated: C, 63.30; H, 7.70; N, 3.69; Found: C, 62.18; H, 7.90; N, 3.63.

EXAMPLE 27

1-[2-(dimethylamino)-1-(3-hydroxyphenyl)ethyl]cyclohexanol

By replacing p-bromophenyl acetic acid with a molar equivalent amount of m-benzyloxyphenyl acetic acid in Example 13, and following the procedures described in Example 14 and 15, 1-[1-(3-benzyloxyphenyl)-2-(dimethylamino)ethyl]cyclohexanol was obtained.

Hydrogenolysis of this product (2.3 g) was conducted in 200 ml ethanol employing a Paar bomb, 300 mg. 10% Pd/C until uptake of hydrogen ceased. The catalyst was removed by filtration and the solvent evaporated to afford a solid product which was converted to its hydrochloride salt with 5N isopropanolic hydrochloride, m.p. 162°–164° C.

Analysis for: $C_{16}H_{25}NO_2 \cdot HCl$; Calculated: C, 64.08; H, 8.74; N, 4.67; Found: C, 62.78; H, 8.55; N, 4.55.

EXAMPLE 28

1-[1-(4-bromophenyl)-2-(dimethylamino)ethyl]cyclobutanol

By replacing cyclohexanone in Example 14 with a molar equivalent amount of cyclobutanone and following the procedure described in Example 15, 1-[1-(4-bromophenyl)-2-(dimethylamino)ethyl]cyclobutanol was obtained. It was converted to the hydrochloride salt, m.p. 220°–222° C.

Analysis for: $C_{14}H_{20}NOBr \cdot HCl$; Calculated: C, 50.22; H, 6.28; N, 4.19; Found: C, 50.26; H, 6.11; N, 4.13.

EXAMPLE 29

1-[2-(dimethylamino)-1-(4-methoxyphenyl)ethyl]cyclopentanol

By replacing p-bromophenylacetic acid with a molar equivalent amount of p-methoxyphenyl acetic acid in Example 13, 4-methoxy-N,N-dimethylbenzene acetamide was obtained. Subsequently, following the procedure outlined in Example 14, replacing cyclohexanone with a molar equivalent amount of cyclopentanone, there was obtained the corresponding cyclopentanol derivative. This intermediate was converted, following the procedure described in Example 15, to the title compound as the hydrochloride, m.p. 194° C.

Analysis for: $C_{16}H_{25}NO_2 \cdot HCl$; Calculated: C, 64.07; H, 8.76; N, 4.67; Found: C, 64.19; H, 8.72; N, 4.33.

EXAMPLE 30

1-[2-(dimethylamino)-1-(4-methoxyphenyl)ethyl]cycloheptanol

By replacing cyclopentanone with a molar equivalent of cycloheptanone in Example 27, the title compound was obtained as the hydrochloride, m.p. 175°–177° C.

Analysis for: $C_{18}H_{29}NO_2 \cdot HCl \cdot 1/4H_2O$; Calculated: C, 65.03; H, 9.26; N, 4.21; Found: C, 65.25; H, 9.16; N, 4.29.

EXAMPLE 31

1-[2-(dimethylamino)-1-(4-methoxyphenyl)ethyl]cyclooctanol

By replacing cyclopentanone with a molar equivalent amount of cyclooctanone in Example 29, the title compound was obtained as the hydrochloride, m.p. 178°–180° C.

Analysis for: $C_{19}H_{31}NO_2 \cdot HCl \cdot 1/4H_2O$; Calculated: C, 65.87; H, 9.48; N, 4.04; Found: C, 65.79; H, 9.08; N, 3.95.

EXAMPLE 32

1-[2-(dimethylamino)-1-(4-methoxyphenyl)ethyl]cyclohex-2-en-1-ol

By replacing 4-bromo-N,N-dimethylbenzeneacetamide with a molar equivalent of 4-methoxy-N,N-dimethylbenzeneacetamide in Example 14, and cyclohexanone with 2-cyclohexen-1-one, was obtained the corresponding cyclohexenone derivative. This intermediate was converted following the procedure described in Example 15 to the title compound as the fumarate, m.p. 128°–130° C.

Analysis for: $C_{17}H_{25}NO_2 \cdot C_4H_4O_4$; Calculated: C, 64.4; H, 7.31; N, 3.58; Found: C, 63.8; H, 7.46; N, 3.88.

EXAMPLE 33

Resolution of Racemic 1-[2-(dimethylamino)-1-(4-methoxyphenyl)ethyl]cyclohexanol 1-[2-(dimethylamino)-1-(4-methoxyphenyl)ethyl]cyclohexanol (48.0 g., 0.173 m) dissolved in ethyl acetate (350 ml) was treated with di-p-toluoyl-d-tartaric acid (33.5 g., 0.082 m) dissolved in ethyl acetate (250 ml). After standing overnight, the solid was filtered. The solid was recrystallized three times by dissolving in boiling ethyl acetate (300 ml) and methanol (50 ml), concentrating by boiling to incipient crystallization and chilling. Yield 31.7 g., m.p. 126°–128° C. $[\alpha]_D^{25} = -50.51$; c = 1.03 ethanol.

The salt was converted to its free base by shaking in 2N sodium hydroxide and diethyl ether. The ether layer was washed with brine, dried over anhydrous sodium carbonate, evaporated and dried in vacuo. Yield 16.4 g., 68.5%. m.p. 104°–5° C. $[\alpha]_D^{25} = +27.95$; c = 1.15, 95% ethanol.

The base was dissolved in ether (500 ml) and treated with 4.5N hydrogen chloride in isopropanol (20 ml). The resulting hydrochloride salt was recrystallized from warm methanol (75 ml) by dilution with ether (400 ml) and chilling. Yield 16.6 g. m.p. 239°–241° C. $[\alpha]_D^{25} = -4.38$; c = 1.01, 95% ethanol.

The filtrate and washings from the original di-p-toluoyl-d-tartrate salt were evaporated to dryness. The free base was obtained by shaking the solid with 2N sodium hydroxide (400 ml), extracting with diethyl ether (3×250 ml), washing the extracts with brine and drying. Yield 24.2 g. The base was dissolved in ethyl acetate (150 ml) and treated with di-p-toluoyl-l-tartaric acid (16.75 g, 0.0435 m) dissolved in ethyl acetate (150 ml). After standing overnight the salt was filtered and was recrystallized twice from ethyl acetate (300 ml) and methanol (50 ml) as described. Yield 29.4 g. m.p. 124°–127° C. $[\alpha]_D^{25} = +50.77$, c = 0.845 ethanol.

The base was obtained in the manner described. Yield 14.7 g. m.p. 104°–105° C. $[\alpha]_D^{25} = -26.56$, c=1.22%, 95% ethanol.

The free base was converted to the hydrochloride salt.

Yield 14.5 g. m.p. 239°–241° C. $[\alpha]_D^{25} = +4.98$, c=1.01, 95% ethanol.

EXAMPLE 34

1-[1-(4-aminophenyl)-2-dimethylaminoethyl]cyclohexanol 17.0 g (0.095 moles) of p-aminophenylacetic acid, dimethylamide was dissolved in 500 ml of tetrahydrofuran, placed under a nitrogen atmosphere, and cooled to −20° C. 23.6 g (1.15 equivalents) of 1,1,4,4-tetramethyl-1,4-dichlorosilylethylene was added, followed dropwise by a solution of 42 g (2.4 equivalents) of sodium bis(trimethylsilyl)amide in 250 ml of THF. The mixture was allowed to warm to room temperature and was stirred for 18 hours.

The mixture was next cooled to −78° C. and 71.6 ml (1.2 equivalents) of 1.6N n-butyl lithium in hexane added. The reaction was stirred for 45 minutes and then 20 ml (2.0 equivalents) of cyclohexanone added. The mixture was stirred for an additional 1 hour at −78° C. and then poured into a saturated aqueous solution of ammonium chloride. The organic phase was removed and the aqueous phase was extracted with diethyl ether. The combined organic phases were dried over sodium sulfate, filtered and concentrated in vacuo to yield 20 g of crude 1-[(4-aminophenyl)(dimethylaminocarbonyl)-methyl]cyclohexanol. Column chromatography on silica gel with 1% methanol in methylene chloride gave 16 g of essentially pure white solid. A sample twice recrystallized from ethanol had m.p. 169°–170° C. and the following elemental analysis:

Analysis for: $C_{16}H_{24}O_2N_2$; Calculated: C, 69.51; H, 8.77; N, 10.14; Found: C, 69.69; H, 8.96; N, 10.26.

5.0 g (0.018 mole) of the above amide was dissolved in 300 ml of dry tetrahydrofuran and added dropwise to a mixture of 1.1 g of lithium aluminum hydride and 8.0 ml of concentrated sulfuric acid in 200 ml of tetrahydrofuran at 0° C. The mixture was stirred at 0° C. for five hours, then the excess reagent was destroyed by the dropwise addition of 4 ml of 50:50 THF-water, then 4 ml of 15% aqueous sodium hydroxide and finally 4 ml of water. The mixture was filtered and the precipitate washed several times with THF. The combined filtrates were evaporated and the residue recrystallized from isopropanol to give 3.8 g of the title compound as the free base. Treatment with excess oxalic acid in ethyl acetate gave the dioxalate, m.p. 105° C.(d).

Analysis for: $C_{20}H_{30}N_2O_9$; Calculated: C, 54.28; H, 6.84; N, 6.33; Found: C, 53.96; H, 6.83; N, 6.24.

EXAMPLE 35

1-[1-(4-nitrophenyl)-2-dimethylaminoethyl]cyclohexanol 2.0 g (7.6 mmoles) of 1-[1-(4-aminophenyl)-2-dimethylaminoethyl]cyclohexanol was dissolved in 50 ml of methylene chloride and added dropwise to a stirring solution of 2.2 g (2.5 equivalents) of nitrosonium tetrafluoroborate. The reaction was stirred at room temperature for four hours. The methylene chloride was then removed in vacuo and replaced with 100 ml of water. This solution was added slowly to a mixture of 2.0 g of copper in 200 ml of 1N sodium nitrite and the combination stirred for 2 hours at room temperature. Extraction with methylene chloride, drying, and evaporation in vacuo yielded 2.0 g of the free base of the title compound. Recrystallization from isopropanolic HCl gave the hydrochloride, m.p. 211°–212° C.

Analysis for: $C_{16}H_{24}O_3N_2$; Calculated: C, 58.42; H, 7.37; N, 8.52; Found: C, 58.03; H, 7.53; N, 8.69.

EXAMPLE 36

1-[2-dimethylamino)-1-(3-bromo-4-methoxyphenyl)ethyl]cyclohexanol

By replacing 1-[2-amino-1-(p-methoxyphenyl)ethyl]cyclohexanol in Example 3 with a molar equivalent amount of 1-[2-amino-1-(3-bromo-4-methoxyphenyl)ethyl]cyclohexanol and refluxing overnight, the title compound was obtained, m.p. 218°–220° C.

Analysis for: $C_{17}H_{26}NO_2Br.HCl$; Calculated: C, 57.98; H, 6.92; N, 3.56; Found: C, 51.57; H, 6.79; N, 3.46.

EXAMPLE 37

2-[1-(dimethylamino)-2-(4-methoxyphenyl)propyl]cyclohexanol 14.7 g (0.10 mole) of p-methoxyphenylacetonitrile was dissolved in 250 ml of dry tetrahydrofuran and placed in a dry ice/isopropanol bath under $N_2$. 69.0 ml of 1.6M n-butyl lithium (0.11 mole) was added dropwise over 30 minutes and the mixture stirred at −78° C. for one hour. The lithium salt of the nitrile precipitated as a yellow solid during this time. 71.0 g (0.50 mole) of methyl iodide was then added and stirring at −78° C. continued for an additional hour. The mixture was then poured into saturated ammonium chloride and the product extracted into diethyl ether, washed with saturated sodium chloride and dried over sodium sulfide. It was filtered and evaporated, redissolved in methylene chloride and passed through Florisel ®. Evaporation gave 15.0 g of α-(p-methoxyphenyl)propionitrile as an orange oil.

The α-(p-methoxyphenyl)propionitrile prepared above was redissolved in 250 ml of tetrahydrofuran and cooled to −78° C. in dry ice/isopropanol. 69.0 ml of 1.6M n-butyllithium was added over 30 minutes and the mixture stirred for 1 hour under nitrogen. 20 ml of cyclohexanone was then added and stirring at 078° C. was continued for an additional hour. The mixture was poured into saturated ammonium chloride solution and the product extracted with diethyl ether. It was washed with water, saturated sodium chloride and dried over sodium sulfate. Filtration and evaporation gave 21.5 g of white solid. A sample twice recrystallized from benzene had m.p. 129° C. and the following analysis:

Analysis for: $C_{16}H_{21}NO_2$; Calculated: C, 74.10; H, 8.16; N, 5.40; Found: C, 73.95; H, 8.04; N, 5.29.

4.0 g (15 mmoles) of the β-hydroxynitrile prepared above was dissolved in 200 ml of tetrahydrofuran and 50 ml of 1M borane tetrahydrofuran complex was added. The mixture was refluxed for 2 hours and allowed to cool. 200 ml of 2N HCl was added and the THF removed in vacuo. The aqueous solution was made basic by the addition of solid potassium carbonate and the product extracted with 500 ml of ethyl acetate, washed with saturated sodium chloride and dried over sodium sulfate. This was filtered and evaporated and treated with isopropanolic HCl and diethyl ether to yield 3.3 g of the primary amine, m.p. 209° C.

Analysis for: $C_{16}H_{26}NO_2Cl$; Calculated: C, 64.09; H, 8.74; N, 4.67; Found: C, 63.70; H, 8.60; N, 4.59.

3.0 g (10 mmole) of the primary amine hydrochloride was dissolved in 200 ml of absolute ethanol. 5.0 ml of 37% aqueous formaldehyde and 1.0 g of 10% palladium on carbon were added and the mixture was treated with 50 psi of hydrogen on a Parr shaker for 3 days. The mixture was then filtered and evaporated and the solvent replaced with 300 ml of water and washed with 300 ml of ethyl acetate. The aqueous solution was then made pasic with solid sodium carbonate and again extracted with ethyl acetate. The organic extract was washed with saturated brine and dried over sodium sulfate. It was filtered and evaporated and the title compound precipitated as the hydrochloride from isopropanol/ether by the addition of isopropanolic HCl. A second crystallization from isopropanol gave 2.0 g of white solid, m.p. 271° C.

EXAMPLE 38

By following a procedure similar to Examples 13 to 15, using (a) 3,4-dibromophenylacetic acid, (b) 3-methylphenylacetic acid, (c) 4-bromophenylacetic acid and (d) 3-methoxyphenylacetic acid instead of p-bromophenylacetic acid and, as the cycloalkanone, (a) cyclohexanone, (b) cyclohexanone, (c) cyclobutanone and (d) cyclopentanone, there are prepared (a) 1-[1-(3,4-dibromophenyl)-2-(dimethylamino)ethyl]cyclohexanol, (b) 1-[2-(dimethylamino)-1-(3-methylphenyl)ethyl]cyclohexanol, (c) 1-[1-(4-bromophenyl)-2-(dimethylamino)ethyl]cyclobutanol and (d) 1-[2-(dimethylamino)-1-(3-methoxyphenyl)ethyl]cyclopentanol.

What is claimed is:
1. A compound of the formula:

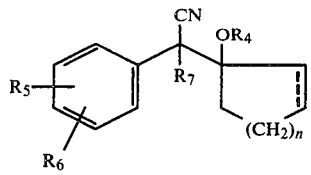

in which the dotted line represents optional unsaturation, and $R_4$ is hydrogen or alkyl of 1 to 6 carbon atoms;

$R_5$ and $R_6$, one of which may be hydrogen, are ortho or para substituents, independently selected from the group consisting of hydroxyl, alkyl of 1 to 6 carbon atoms, alkoxy of 1 to 6 carbon atoms, aralkoxy of 7 to 9 carbon atoms, alkanoyloxy of 2 to 7 carbon atoms, alkylmercapto of 1 to 6 carbon atoms, halo or trifluoromethyl;

$R_7$ is hydrogen or alkyl of 1 to 6 carbon atoms; and n is one of the integers 0, 1, 2, 3 or 4.

2. The compound of claim 1 which is 1-[cyano(p-methoxyphenyl)methyl]cyclohexanol.

3. The compound of claim 1 which is 1-[cyano(p-chlorophenyl)methyl]cyclohexanol.

4. The compound of claim 1 which is 1-[cyano(3-bromo-4-methoxyphenyl)methyl]cyclohexanol.

5. The compound of claim 1 which is 1-[2-cyano-2-(4-methoxyphenyl)ethyl]cyclohexanol.

* * * * *